United States Patent [19]

Pastor et al.

[11] Patent Number: 5,230,816
[45] Date of Patent: Jul. 27, 1993

[54] 3,9-BIS(DIALKYLAMINO)-2,4,8,10-TETRAOXA-3,9-DIPHOSPHASPIRO[5.5]UNDECANES AND STABILIZED COMPOSITIONS

[75] Inventors: Stephen D. Pastor, Danbury, Conn.; Paul A. Odorisio, Edgewater, N.J.

[73] Assignee: Ciba-Geigy Corporation, Ardsley, N.Y.

[21] Appl. No.: 878,677

[22] Filed: May 5, 1992

[51] Int. Cl.$^5$ .......................................... C10M 137/16
[52] U.S. Cl. .......................... 252/49.9; 252/400.021; 524/120; 568/12
[58] Field of Search .................. 252/49.9, 400.21; 524/120; 568/12

[56] References Cited

U.S. PATENT DOCUMENTS

| | | |
|---|---|---|
| 3,138,585 | 6/1964 | Ritz et al. |
| 3,141,032 | 7/1964 | Friedman ............... 252/49.8 |
| 3,180,793 | 4/1965 | Ritz. |
| 3,192,243 | 6/1965 | Gaglioni. |
| 4,130,540 | 12/1978 | Valdiaerri et al. |
| 4,661,594 | 4/1987 | Rasberger et al. |
| 4,664,828 | 5/1987 | Jung et al. .............. 252/49.8 |
| 4,701,273 | 10/1987 | Brady et al. ............ 252/49.9 |
| 4,778,613 | 10/1988 | Cherney et al. ......... 252/49.9 |
| 4,798,822 | 1/1989 | Rasberger et al. |
| 4,803,234 | 2/1989 | Cantatore et al. |
| 4,927,925 | 5/1990 | Cantatore et al. |
| 5,077,329 | 12/1991 | Pastor et al. ........... 252/49.9 |

FOREIGN PATENT DOCUMENTS 190748 12/1981 Czechoslovakia.
146464 2/1981 Fed. Rep. of Germany.
2014586 8/1979 United Kingdom.

OTHER PUBLICATIONS

B. A. Arbuzov et al., The Steric Structure of Phosphorus-Containing, Heterocycles Communication 9. Pivawes, et al., Dec. 1967 pp. 599–603, Synthesis and Reactions of 3,9-Diisocyanates and Diisothiocyanates.
Karasei, et al., Polymer Sci. USSR vol. 22, No. 6, pp. 1544–1553 (1980).
Polymer Degradation and Stability 5(1983) 373–397, Holcik, et al.
C.A. vol. 98, 1983.

*Primary Examiner*—Jacqueline V. Howard
*Attorney, Agent, or Firm*—Luther A. R. Hall

[57] ABSTRACT

Compounds of formula I

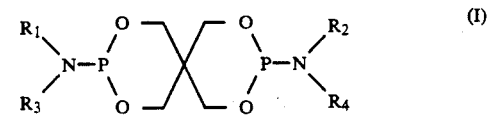

wherein $R_1$, $R_2$, $R_3$ and $R_4$ are each 2-ethylhexyl or are independently higher alkyl, or $R_1$ and $R_2$ are independently hydrogen or methyl, and $R_3$ and $R_4$ are independently higher alkyl are effective processing stabilizers for polymers processed at elevated temperatures by preventing polymer degradation and providing resistance to discoloration. The compounds of formula I also exhibit superior hydrolytic stability and resist moisture pickup on storage.

24 Claims, No Drawings

3,9-BIS(DIALKYLAMINO)-2,4,8,10-TETRAOXA-3,9-DIPHOSPHASPIRO[5.5]UNDECANES AND STABILIZED COMPOSITIONS

The instant invention pertains to new 3,9-bis(dialkylamino-2,4,8,10-tetraoxa,-3,9-diphosphaspiro[5.5]undecane compounds and stabilized compositions containing said compounds.

BACKGROUND OF THE INVENTION

Many compounds of the general structure

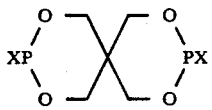

are known and some have been touted as stabilizers for polymers.

The compound where X is anilino is known from U.S. Pat. No. 3,192,243 as a polymer stabilizer.

East German patent No. 146,464 describes compounds where X is NRR' where R and R' are lower alkyl, phenyl, tolyl or cyclohexyl as stabilizers for polymers.

British patent No. 2,014,586 discloses the compound where X is dimethylamino as a chemical intermediate. U.S. Pat. No. 4,130,540 describes compounds where X is dialkylamino, diarylamino, dicycloalkylamino or piperidino as chemical intermediates.

U.S. Pat. Nos. 3,138,585 and 3,180,793 describe compounds where X is aziridinyl as insecticides or textile crosslinking agents.

Czechoslovakian patent No. 190,748 describes compounds where X is dialkykamino, diarylamino or dicycloalkylamino as polymer stabilizers.

Compounds where X is diethylamino are known from academic studies, Izv. Akad. Nauk. S.S.S.R., Serkim, 11, 2485 (1974), and as a vulcanizing agent for fluoro rubber, Vysokomol Soedin, Ser. A. 22, 1404 (1980).

Compounds where X is dicyclohexylamino are shown to be polymer stabilizers in Poly. Degrad. Stab. 5, 373 (1983).

U.S. Pat. Nos. 4,661,594; 4,798,822; 4,803,234 and 4,927,925 and Chem. Abst. 106, 67493p (=Czech. 232,346) describe compounds where X is a substituted hindered amine 4-piperidyl moiety as light stabilizers.

None of these references describe compounds where X is dialkylamino where alkyl is a long chain alkyl of 16 to 30 carbon atoms.

While the instant compound where X is di(2-ethylhexyl)amino is generically encompassed by the references where X is dialkylamino, the specific compound and its outstanding stabilization properties are not described or suggested.

OBJECTS OF THE INVENTION

One object of the instant invention is to provide novel compounds which are 3,9-bis[di(2-ethylhexyl)amino]-2,4,8,10-tetraoxa-3,9-diphosphaspiro[5.5]undecane and 3,9-bis[di(higher alkyl)amino]-2,4,8,10-tetraoxa-3,9-diphosphaspiro[5.5]undecanes.

Another object of the instant invention is to provide organic polymer compositions stabilized against degradation and discoloration during processing at elevated temperatures.

DETAILED DISCLOSURE

The instant invention pertains to a compound of formula I

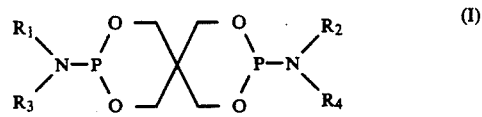

wherein
$R_1$, $R_2$, $R_3$ and $R_4$ are each 2-ethylhexyl; or
$R_1$, $R_2$, $R_3$ and $R_4$ are independently alkyl of 16 to 30 carbon atoms; or
$R_1$ and $R_2$ are independently hydrogen or methyl, and $R_3$ and $R_4$ are independently alkyl of 16 to 30 carbon atoms; or
$R_1$, $R_2$, $R_3$ and $R_4$ are independently a mixture of alkyl, alkenyl and alkadienyl radicals of 16 to 30 carbon atoms.

The instant invention also pertains to a stabilized composition which comprises
(a) an organic material, subject to thermal, oxidative or light-induced degradation, and
(b) an effective stabilizing amount of a compound of formula I as described above.

The instant invention also relates to said composition which additionally contains a phenolic antioxidant or a hindered amine.

Preferably the organic material of the instant invention is an organic polymer or a lubricant or oil.

The instant compositions are particularly utilized when the organic polymer is processed at an elevated temperature.

Particularly preferred organic polymers are the polyolefins, especially polypropylene and polyethylene, and polyamides. Most particularly the organic polymer is polypropylene.

Preferably the compound of formula I is 3,9-bis[di(2-ethylhexyl)amino]-2,4,8,10-tetraoxa-3,9-diphosphaspiro[5.5]undecane; 3,9-bis[di(hydrogenated tallow)amino]-2,4,8,10-tetraoxa-3,9-diphosphaspiro[5.5]undecane; or 3,9-bis[di(tallow)amino]-2,4,8,10-tetraoxa-3,9-diphosphaspiro[5.5]undecane.

Most preferably the compound of formula I is 3,9-bis[di(2-ethylhexyl)amino]-2,4,8,10-tetraoxa-3,9-diphosphaspiro[5.5]undecane.

The compounds of this invention are conveniently prepared by the reaction of a secondary or primary amine, preferably a secondary amine, with 3,9-dichloro-2,4,8,10-tetraoxa-3,9-diphosphaspiro[5.5]undecane. The preparation of this dichloro intermediate is taught by H. J. Lucas et al., J. Am. Chem. Soc., 72, 5491 (1950). The required amines are largely items of commerce.

The compounds of this invention are more effective processing stabilizers for polyolefins than the prior art compounds both in preventing molecular weight changes as well as preventing discoloration. The compounds of this invention also show superior stability during storage in resisting moisture pickup and hydrolysis when compared to the prior art compounds.

Instant compounds of special interest are those where $R_1$, $R_2$, $R_3$ and $R_4$ are independently hexadecyl, heptadecyl, octadecyl, eicosyl or tricontyl. Most preferably $R_1$, $R_2$, $R_3$ and $R_4$ are independently hexadecyl, heptadecyl or octadecyl or the alkyl mixture found in hydrogenated tallow amine.

Other compounds of special interest are those where $R_1$, $R_2$, $R_3$ and $R_4$ are independently hexadecyl, heptadecyl, octadecyl, hexadecenyl, octadecenyl or octadecadienyl or the radical mixture found in tallow amine.

The instant compounds are derived from long chain aliphatic secondary amines such as di(hydrogenated tallow)amine and di(tallow)amine.

A typical di(hydrogenated tallow)amine has the following distribution of alkyl substituents:

| | $R_1R_2NH$ | |
|---|---|---|
| $R_1$ | $R_2$ | % |
| $C_{16}$ | $C_{14}$ | 1.9 |
| $C_{16}$ | $C_{16}$ | 12.4 |
| $C_{16}$ | $C_{17}$ | 2.8 |
| $C_{16}$ | $C_{18}$ | 36.0 |
| $C_{17}$ | $C_{18}$ | 3.9 |
| $C_{18}$ | $C_{18}$ | 39.0 |
| other | | 4.0 |

It is clear that the di(hydrogenated tallow)amine originating from animal sources may well vary somewhat in the specific distribution of alkyl substituents, but the di(hydrogenated tallow)amine contains major amounts of N,N-dihexadecylamine; N,N-dioctadecylamine and N-hexadecyl-N-octadecylamine. The individual components of the mixture can be separated by distillation under high vacuum.

However, for the purpose of this invention, there is no need to carry out such separation and the instant compound prepared from di(hydrogenated tallow)amine represents a preferred embodiment of the instant invention.

In like manner, di(tallow)amine can be used in the instant invention and represents a preferred embodiments of the instant invention.

A typical di(tallow)amine has the following distribution of alkyl, alkenyl and alkadienyl substituents.

| Radical | % |
|---|---|
| hexadecyl | 29.0 |
| heptadecyl | 1.0 |
| octadecyl | 20.5 |
| hexadecenyl | 1.5 |
| octadecenyl and octadecadienyl | 44.0 |
| other | 4.0 |

In general polymers which can be stabilized include
1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under 1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene of methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/vinyl acetate copolymers, or vinyl fluoride/vinyl ether copolymers.

8. Polymers which are derived from $\alpha,\beta$-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadienes with terminal hydroxyl groups on the one side and aliphatic or aromatic polyisocyanates of the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-phenylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as block-copolymer-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolymers of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or polyester acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ether or from cycloaliphatic diepoxides.

26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubber, e.g. natural latex or latices of carboxylated styrene/-butadiene copolymers.

30. Polysiloxanes such as the soft, hydrophilic polysiloxanes described, for example, in U.S. Pat. No. 4,259,467; and the hard polyorganosiloxanes described, for example, in U.S. Pat. No. 4,355,147.

31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.

32. Radiation curable compositions containing ethylenically unsaturated monomers or oligomers and a polyunsaturated aliphatic oligomer.

33. Epoxymelamine resins such as light-stable epoxy resins crosslinked by an epoxy functional coetherified high solids melamine resin such as LSE-4103 (Monsanto).

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

1. Antioxidants 1.1. Alkylated monophenols for example,
2,6-di-tert-butyl-4-methylphenol
2-tert-butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-($\alpha$-methylcyclohexyl)-4,6-dimethylphenol
2,6-di-octadecyl-4-methylphenol
2,4,6-tri-cyclohexylphenol
2,6-di-tert-butyl-4-methoxymethylphenol 1.2. Alkylated hydroquinones for example,
2,6-di-tert-butyl-4-methoxyphenol
2,5-di-tert-butyl-hydroquinone
2,5-di-tert-amyl-hydroquinone
2,6-diphenyl-4-octadecyloxyphenol 1.3. Hydroxylated thiodiphenyl ethers for example,
2,2'-thio-bis-(6-tert-butyl-4-methylphenol)
2,2'-thio-bis(4-octylphenol)
4,4'-thio-bis(6-tert-butyl-3-methylphenol)
4,4'-thio-bis-(6-tert-butyl-2-methylphenol)

1.4. Alkylidene-bisphenols for example,
2,2'-methylene-bis-(6-tert-butyl-4-methylphenol)
2,2'-methylene-bis-(6-tert-butyl-4-ethylphenol)

2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl)-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl] terephthalate.

1.5. Benzyl compounds for example,
1,3,5-tri-(3,5-di-tert-butyl-4-hydroxybenzyl)-2,4,6-trimethylbenzene
di-(3,5-di-tert-butyl-4-hydroxybenzyl) sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl) isocyanurate
1,3,5-tris-(4-tert-butyl-3-hydroxy-2,6-dimethylbenzyl) isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt

1.6. Acylaminophenols for example,
4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate

1.7. Esters of
β-(3,5-di-tert-butyl-4-hydroxyphenyl)-propionic acid with monohydric or polyhydric alcohols for example,

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.8. Esters of
β-(5-tert-butyl-4-hydroxy-3-methylphenyl)-propionic acid with monohydric or polyhydric alcohols for example,

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.9. Amides of
β-(3,5-di-tert-butyl-4-hydroxyphenyl)-propionic acid for example,
N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine

1.10 Diarylamines for example,
diphenylamine, N-phenyl-1-naphthylamine, N-(4-tert-octylphenyl)-1-naphthylamine, 4,4'-di-tert-octyl-diphenylamine, reaction product of N-phenylbenzylamine and 2,4,4-trimethylpentene, reaction product of diphenylamine and 2,4,4-trimethylpentene, reaction product of N-phenyl-1-naphthylamine and 2,4,4-trimethylpentene.

2. UV absorbers and light stabilizers

2.1. 2-(2'-Hydroxyphenyl)-benzotriazoles for example,
the 5'-methyl-,3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxy-octa-(ethyleneoxy)carbonyl-ethyl)-, 3'-dodecyl-5'-methyl-, and 3'-tert-butyl-5'-(2-octyloxycarbonyl)ethyl- and dodecylated-5'-methyl derivatives.

2.2. 2-Hydroxy-benzophenones for example,
the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example,
phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates for example,
α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5. Nickel comounds for example,
nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines for example,
bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentanemethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl) 1,2,3,4-butanetetracarboxylate, 1,1'(1,2-ethanediyl)-bis-(3,3,5,5-tetramethylpiperazinone), bis(1-octyloxy-2,2,6,6-tetramethylpiperidin-4-yl) sebacate.

2.7. Oxalic acid diamides for example,
4,4'-di-octyloxy-oxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis(3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy- as well as of o- and p-ethoxy-disubstituted oxanilides.

2.8. Hydroxyphenyl-s-triazines, for example
2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4-(2-hydroxy-4-(2-hydroxyethoxy)phenyl]-6-(2,4-dimethylphenyl)-s-triazine; 2,4-bis[2-hydroxy-4-(2-hydroxyethoxy)-phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal deactivators for example,
N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)hydrazine, 3-salicyloylamino-1,2,4-triazole, bis-benzylidene-oxalic acid dihydrazide.

4. Phosphites and phosphonites for example,
triphenyl phosphite, diphenylalkyl phosphites, phenyldialkyl phosphites, tri-(nonylphenyl) phosphite, trilauryl phosphite, trioctadecyl phosphite, di-stearylpentaerythritol diphosphite, tris-(2,4-di-tert-butylphenyl) phosphite, di-isodecylpentaerythritol diphosphite, di-(2,4-di-tert-butylphenyl)pentaerythritol diphosphite, tristearylsorbitol triphosphite, tetrakis-(2,4-di-tert-butylphenyl) 4,4'-diphenylylenediphosphonite.

5. Compounds which destroy peroxide for example
esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines for example
N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Nitrones for example
N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alphaheptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.

8. Polyamide stabilizers for example copper salts in combination with iodides and/or phosphorus compounds and salts of divalent manganese.

9. Basic co-stabilizers for example,
melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleating agents for example,
4-tert-butyl-benzoic acid, adipic acid, diphenylacetic acid.

11. Fillers and reinforcing agents for example, calcium carbonate, silicates, glass fibers, asbestos, talc, kaolin, mica, barium sulfate, metal oxides and hydroxides carbon black, graphite.

12. Other additives for example, plasticizers, lubricants, emulsifiers, pigments, optical brighteners, flameproofing agents, anti-static agents, blowing agents and thiosynergists such as dilauryl thiodipropionate or distearyl thiodipropionate.

The phenolic antioxidant of particular interest is selected from the group consisting of n-octadecyl 3,5-di-tert-butyl-4-hydroxyhydrocinnamate, neopentanetetrayl tetrakis(3,5-di-tert-butyl-4-hydroxyhydrocinnamate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6-dioxaoctamethylene bis(3-methyl-5-tert-butyl-4-hydroxyhydrocinnamate), 2,6-ditert-butyl-p-cresol, 2,2'-ethylidene-bis(4,6-di-tert-butylphenol), 1,3,5-tris(2,6-dimethyl-4-tert-butyl-3-hydroxybenzyl)isocynurate, 1,1,3-tris(2-methyl-4-hydroxy-5-tert-butylphenyl)butane, 1,3,5-tris[2-(3,5-di-tert-butyl-4-hydroxyhydrocinnamoyloxy)ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)-ethyl]-oxamide.

A most preferred phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-tri-methyl-2,4,6-tris(3,5-di-tert-butyl-4-hydroxybenzyl)benzene, 1,3,5-tris(3,5-di-tert-butyl-4-hydroxybenzyl)isocyanurate, 2,6-di-tert-butyl-p-cresol or 2,2'-ethylidene-bis(4,6-di-tertbutylphenol).

The hindered amine compound of particular interest is selected from the group consisting of
bis(2,2,6,6-tetramethylpiperidin-4-yl) sebacate,
bis(1,2,2,6,6-pentamethylpiperidin-4-yl) sebacate,
di(1,2,2,6,6-pentamethylpiperidin-4-yl) (3,5-di-tert-butyl-4-hydroxybenzyl)butylmalonate,
4-benzoyl-2,2,6,6-tetramethylpiperidine, 4-stearyloxy-2,2,6,6-tetramethylpiperidine,
3-n-octyl-7,7,9,9-tetramethyl-1,3,8-triaza-spiro[4.5]decane-2,4-dione,
tris(2,2,6,6-tetramethylpiperidin-4-yl) nitrilotriacetate,
1,2-bis(2,2,6,6-tetramethyl-3-oxopiperazin-4-yl)ethane,
2,2,4,4-tetramethyl-7-oxa-3,20-diaza-21-oxodispiro[5.1.11.2] heneicosane, polycondensation product of 2,4-dichloro-6-tert-octylamino-s-triazine and 4,4'-hexamethylenebis(amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylenebis-(amino-2,2,6,6-tetra-methylpiperidine) and 1,2-dibromoethane,
tetrakis(2,2,6,6-tetramethylpiperidin-4-yl) 1,2,3,4-butanetetracarboxylate, tetrakis(1,2,2,6,6-pentamethylpiperidin-4-yl) 1,2,3,4-butanetetracarboxylate, polycondensation product of 2,4-dichloro-6-morpholino-s-triazine and
4,4'-hexamethylenebis(amino-2,2,6,6-tetramethylpiperidine), N,N',N'',N'''-tetrakis[(4,6-bis(butyl-2,2,6,6-tetramethyl-piperidin-4-yl)-amino-s-triazin-2-yl]-1,10-diamino-4,7-diazadecane, mixed [2,2,6,6-tetramethyl-piperidin-4-yl/β,β,β',β'-tetramethyl-3,9-(2,4,8,10-tetraoxaspiro[5.5]-undecane)diethyl]1,2,3,4-butanetetracarboxylate,
mixed [1,2,2,6,6-pentamethylpiperidin-4-yl/β,β,β',β'-tetramethyl-3,9-(2,4,8,10-tetraoxaspiro[5.5]-undecane)diethyl]1,2,3,4-butanetetracarboxylate, octamethylene bis(2,2,6,6-tetramethylpiperidin-4-carboxylate),
4,4'-ethylenebis(2,2,6,6-tetramethylpiperazin-3-one), and
bis(1-octyloxy-2,2,6,6-tetramethylpiperidin-4-yl) sebacate.

A most preferred hindered amine compound is bis(2,2,6,6-tetramethylpiperidin-4-yl) sebacate, the polycondensation product of 1-(2-hydroxyethyl)-2,2,6,6-tetramethyl-4-hydroxypiperdine and succinic acid, the polycondensation product of 2,4-dichloro-6-tert-octylamino-s-triazine and 4,4'-hexamethylenebis-(amino-2,2,6,6-tetramethylpiperidine), N,N',N'',N'''-tetrakis[(4,6-bis(butyl-(2,2,6,6-tetramethyl-piperidin-4-yl)amino)-s-triazine-2-yl]-1,10-diamino-4,7-diazadecane or bis(1-octyloxy-2,2,6,6-tetramethylpiperidin-4-yl) sebacate.

The lubricating oil may be a mineral oil, a synthetic oil or any mixture of such oils. Mineral oils are preferred and examples of these include paraffinic hydrocarbon oils e.g. a mineral oil having a viscosity of 46 $mm^2/s$ at 40° C.; "150 Solvent Neutral" a solvent refined neutral mineral oil having a viscosity of 32 $mm^2/s$ at 40° C.; and "solvent bright-stocks", a high boiling residue from the process of refining mineral oil, and having a viscosity of 46 $mm^2/s$ at 40° C.

Synthetic lubricating oils which may be present may be synthetic hydrocarbons such as polybutenes, alkyl benzenes and poly-alpha olefins as well as simple di-, tri- and tetra-esters, complex esters and polyesters derived from carboxylic acid esters of formula: $G_1$-OCC-alkylene-COO$G_2$ wherein "alkylene" denotes an alkylene residue having from 2 to 14 carbon atoms and $G_1$ and $G_2$ are the same or different and each is an alkyl group having from 6 to 18 carbon atoms. Tri-esters which are of use as lubricating oil base stocks are those derived from trimethylolpropane and $C_6$–$C_{18}$ mono-carboxylic acids or mixtures thereof, whereas suitable tetra-esters include those derived from pentaerythritol and a $C_6$–$C_{18}$ mono-carboxylic acid or mixtures thereof.

Complex esters suitable for use as components of the composition of the present invention are those derived from monobasic acids, dibasic acids and polyhydric alcohols, for instance the complex ester derived from trimethylol propane, caprylic acid and sebacic acid.

Suitable polyesters are those derived from any aliphatic dicarboxylic acid having from 4 to 14 carbon atoms and at least one aliphatic dihydric alcohol having from 3 to 12 carbon atoms, e.g. those derived from azelaic acid or sebacic acid and 2,2,4-trimethylhexane-1,6-diol.

Other lubricating oils are those known to the art-skilled and described e.g. in Schewe-Kobek, "Schmiermittel-Taschenbuch", (Huethig Verlag, Heidelberg 1974), and in D. Klamann, "Schmierstoff und verwandte Produkte", (Verlag Chemie, Weinheim 1982).

The lubricating oils applicational media can also contain other additives which may be added to improve the base properties of lubricants e.g. metal passivators, viscosity-index improvers, pour-paint depressants, dispersing agents, detergents, additional rust inhibitors, extreme pressure additives, anti-wear additives and antioxidants.

Examples of phenolic antioxidants

1. Alkylated Monophenols 2,6-Di-tert-butyl-4-methylphenol, 2,6-di-tert-butylphenol, 2-tert-butyl-4,6-dimethylphenol,2,6-di-tert-butyl-4-ethyl-phenol, 2,6-di-tert-butyl-4-n-butyl-phenol, 2,6-di-tert-butyl-4-i-butylphenol, 2,6-di-cyclopentyl-4-methylphenol, 2-(β-methylcyclohexyl)- 4,6-dimethylphenol, 2,6-di-octa-decyl-4-methyl-phenol, 2,4,6-tri-cyclohexylphenol, 2,6-di-tert-butyl-4-methoxymethylphenol, o-tert-butylphenol.

2. Alkylated Hydroquinones 2,6-Di-tert-butyl-4-methoxyphenol, 2,5-di-tert-butyl-hydroquinone, 2,5-di-tert-amyl-hydroquinone, 2,6-diphenyl-4-octa-decyloxyphenol.

3. Hydroxylated Thiodiphenylethers 2,2'-Thio-bis-(6-tert-butyl-4-methylphenol), 2,2'-thio-bis-(4-octyl-phenyl), 4,4'-thio-bis-(6-tert-butyl-3-methylphenol), 4,4'-thio-bis-(6-tert-butyl-2-methylphenol).

4. Alkylidene-Bisphenols 2,2'-Methylene-bis-(6-tert-butyl-4-methylphenol), 2,2'-methylene-bis-(6-tert-butyl-4-ethylphenol), 2,2'-methylene-bis-(4-methyl-6-(α-methyl-cyclohexyl)-phenol), 2,2'-methylene-bis-(4-methyl-6-cyclohexylphenol), 2,2'-methylene-bis-(6-nonyl-4-methylphenol), 2,2'-methylene-bis-(4,6-di-tert-butylphenol), 2,2'-ethylidene-bis-(4,6-di-tert-butylphenol), 2,2'-ethylidene-bis-(6-tert-butyl-4- or -5-isobutyl-phenol), 2,2'-methylene-bis-(6-(α-methylbenzyl-4-nonylphenol), 2,2'-methylene-bis-(6-(α,α-di-methylbenzyl)-4-nonyl-phenol), 4,4'-methylene-bis-(2,6-di-tert-butyl-phenol), 4,4'-methylene-bis-(6-tert-butyl-2-methylphenol), 1,1-bis-(5-tert-butyl-4-hydroxy-2-methyl-phenol)-butane, 2,6-di-(3-tert-butyl-5-methyl-2-hydroxy-benzyl)-4-methyl-phenol, 1,1,3-tris-(5-tert-butyl-4-hydroxy-2-methylphenyl)-3-n-dodecyl)-mercaptobutane, ethyleneglycol-bis-[3,3-bis-(3'-tert-butyl-4'-hydroxyphenyl)-butyrate], bis-(3-tert-butyl-4-hydroxy-5-methylphenyl)-dicyclopentadiene, bis-[2-(3'-tert-butyl-2'-hydroxy-5'-methyl-benzyl)-6-tert-butyl-4-methyl-phenyl]-terephthalate.

5. Benzyl Compounds 1,3,5-Tri-(3,5-di-tert-butyl-4-hydroxybenzyl)-2,4,6-trimethyl-benzene, bis(3,5-di-tert-butyl-4-hydroxybenzyl)-sulfide, 3,5-di-tert-butyl-4-hydroxybenzyl-mercaptoacetic acid-isooctylester, bis-(4-tert-butyl-3-hydroxy-2,6-dimethyl-benzyl)dithiolterephthalate, 1,3,5-tris-(3,5-di-tert-butyl-4-hydroxybenzyl)-isocyanurate, 1,3,5-tris-(4-tert-butyl-3-hydroxy- 2,6-dimethyl-benzyl)-isocyanurate, 3,5-di-tert-butyl-4-hydroxybenzyl-phosphonic acid-dioctadecylester, 3,5-di-tert-butyl-4-hydroxybenzyl-phosphonic acid-monoethylester, calcium-salt.

6. Acylaminophenols

4-Hydroxy-lauric acid anilide, 4-hydroxy-stearic acid anilide, 2,4-bis-octylmercapto-6-(3,5-di-tert-butyl-4-hydroxyanilino)-s-triazine, N-(3,5-di-tert-butyl-4-hydroxyphenyl)-carbamic acid octyl ester.

7. Esters of β-(3,5-Di-tert-butyl-4-hydroxyphenyl)-propionic acid with mono- or polyhydric alcohols, for example with methanol, isooctyl alcohol, 2-ethylhexanol, diethylene glycol, octadecanol, triethylene glycol, 1,6-hexanediol, pentaerythritol, neopentyl glycol, tris-hydroxyethyl isocyanurate, thiodiethylene glycol, bis-hydroxyethyl-oxalic acid diamide.

8. Esters of β-(5-tert-butyl-4-hydroxy-3-methylphenyl)-propionic acid with mono- or polyhydric alcohols, for example with methanol, isooctyl alcohol, 2-ethylhexanol, diethylene glycol, octadecanol, triethylene glycol, 1,6-hexanediol, pentaerythritol, neopentyl glycol, tris-hydroxyethyl isocyanurate,thiodiethylene glycol, di-hydroxyethyl-oxalic acid diamide.

9. Amides of β-(3,5-Di-tert-butyl-4-hydroxyphenyl)-propionic acid for example N,N'-Bis-(3,5-di-tert-butyl-4-hydroxyphenylpropionyl)-hexamethylene-diamine, N,N'-bis-(3,5-di-tert-butyl-4-hydroxy-phenylpropionyl)-trimethylene-diamine, N,N'-bis(3,5-di-tert-butyl-4-hydroxyphenylpropionyl)-hydrazine.

Examples of amine antioxidants

N,N'-Di-isopropyl-p-phenylenediamine, N,N'-di-sec.-butyl-p-phenylenediamine, N,N'-bis(1,4-dimethyl-pentyl)-p-phenylenediamine, N,N'-bis(1-ethyl-3-methyl-pentyl)p-phenylenediamine, N,N'-bis(1-methyl-heptyl)-p-phenylenediamine, N,N'-dicyclohexyl-p-phenylenediamine, N,N'-diphenyl-p-phenylenediamine, N,N'-di-(naphthyl-2-)-p-phenylenediamine, N-isopropyl-N'-phenyl-p-phenylenediamine, N-(1,3-dimethylbutyl)-N' -phenyl-p-phenylenediamine, N-(1-methyl-heptyl)-N'-phenyl-p-phenylene-diamine, N-cyclohexyl-N'-phenyl-p-phenylenediamine, 4-(p-toluene-sulfonamido)-diphenylamine, N,N'-dimethyl-N,N'-di-sec-butyl-p-phenylenediamine, di-phenylamine, N-allyldiphenylamine, 4-isopropoxy-diphenylamine, N-phenyl-1-naphthylamine, N-phenyl-2-naphthylamine, octylated diphenylamine, e.g. p,p'-di-tert-octyldiphenylamine, 4-n-butylaminophenol, 4-butyrylamino-phenol, 4-nonanoylamino-phenol, 4-dodecanoyl-amino-phenol, 4-octadecanoyl-amino-phenol, di-(4-methoxy-phenyl)-amine, 2,6-di-tert-butyl-4-dimethyl-amino-methyl-phenol, 2,4'-diamino-diphenylmethane, 4,4'-diaminodiphenyl-methane, N,N,N',N'-tetramethyl-4,4'-diamino-diphenylmethane, 1,2-di-(phenylamino)-ethane, 1,2-di-[2-methyl-phenyl)-amino]-ethane, 1,3-di-(phenylamino)-propane, (o-tolyl)-biguanide, di-[4-1',3'-dimethyl-butyl-phenyl]amine, tert-octylated N-phenyl-1-naphthylamine, mixture of mono- and dialkylated tert-butyl-tert-octyldiphenylamines, 2,3-dihydro-3,3-dimethyl-4H-1,4-benzothiazine, phenothiazine, N-allylphenothiazine, tert-octylated phenothiazine, 3,7-di-tert-octylphenothiazine.

Examples for other antioxidants

Aliphatic or aromatic phosphites, esters of thiodipropionic acid or of thiodiacetic acid, or salts of dithiocarbamic or dithiophosphoric acid.

Examples of metal passivators, for example for copper, are

Triazoles, benzotriazoles and derivatives thereof, tolutriazole and derivatives thereof, e.g. di(2-ethylhexyl)-aminomethyltolutriazole, 2-mercaptobenzothiazole, 5,5'-methylene-bis-benzotriazole, 4,5,6,7-tetrahydrobenzo-triazole,
salicyclidene-propylene-diamine and salicyclaminoguanidine and salts thereof, 1,2,4-triazole and N,N'-disubstituted aminomethyl triazoles of formula

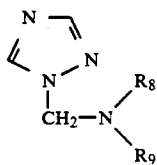

in which $R_8$ and $R_9$ are, independently, e.g. alkyl, alkenyl, or hydroxyethyl, obtained by reacting 1,2,4-triazole with formaldehyde and an amine, $HNR_8R_9$, as disclosed in European Patent Application No. 160620; and the Mannich reaction products derived from benzotriazole or tolutriazole, formaldehyde and an amine $HNR_8R_9$.

Examples of rust inhibitors are a) Organic acids, their esters, metal salts and anhydrides, e.g. N-oleoyl-sarcosine, sorbitan-mono-oleate, lead-naphthenate, alkenyl-succinic acids and -anhydrides, e.g. dodecenyl-succinic acid anhydride, succinic acid partial esters and amines, 4-nonyl-phenoxy-acetic acid.
b) Nitrogen-containing compounds, e.g. I. Primary, secondary or tertiary aliphatic or cycloaliphatic amines and amine-salts of organic and inorganic acids, e.g. oil-soluble alkyl-ammonium carboxylates II. Heterocyclic compounds, e.g. substituted imidazolines and oxazolines.
c) Phosphorus-containing compounds, e.g. amine salts of phosphonic acid or phosphoric acid partial esters, zinc dialkyldithio phosphates.
d) Sulfur-containing compounds, e.g. barium-dinonyl-naphthalene-n-sulfonates, calcium petroleum sulfonates.
e) Derivatives of gamma-alkoxypropylamines described in Japanese Patent Publication No. 15783/1973; and
f) Salts having the formula $Y—NH_3—R_{10}CO_2—$ in which Y is a group $R_{11}X_1CH_2CH(OH)CH_2$ in which $R_{10}$ and $R_{11}$, independently, are e.g. alkyl and $X_1$ is O, $CO_2$, NH, N(alkyl), N(alkenyl) or S, these salts being prepared by mixing an amine $Y—NH_2$ with an acid $R_{10}CO_2H$, as disclosed in DE-OS 3437 876 (German Offenlegungsschrift).
g) Compounds having the formula $$R_{12}—X_2—CH_2—CH(OH)—CH_2NR_{13}R_{14}$$

in which $X_2$ is —O—, —S—, —$SO_2$—C(O)—O— or —N(Rd) in which $R_{12}$ is H or $C_1-C_{12}$alkyl, $R_{13}$ is unsubstituted $C_1-C_4$alkyl or $C_2-C_5$alkyl substituted by one to three hydroxyl groups, $R_{14}$ is hydrogen, unsubstituted $C_1-C_4$alkyl or $C_2-C_5$alkyl substituted by one to three hydroxyl groups provided that at least one of $R_{13}$ and $R_{14}$ is hydroxy-substituted, and $R_{12}$ is $C_2-C_{20}$alkyl —$CH_2$—CH(OH)—$CH_2NR_{13}R_{14}$ or $R_{12}$ is $C_2-C_{18}$alkenyl, $C_2-C_3$alkynyl or $C_5-C_{12}$cycloalkyl provided that, when $X_2$ is —O— or —C(O)—O—, $R_{12}$ is branched $C_4-C_{20}$alkyl. These compounds are described in GB Patent Specification 2172284A.
h) Compounds having the formula:

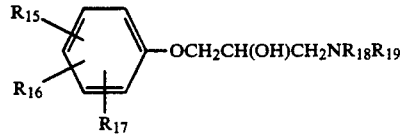

in which $R_{15}$, $R_{16}$, $R_{17}$ are, independently, hydrogen, $C_1-C_{15}$alkyl, $C_5-C_{12}$cycloalkyl, $C_6-C_{15}$aryl or $C_7-C_{12}$aralkyl and $R_{18}$ and $R_{19}$, independently, are hydrogen, 2-hydroxyethyl or 2-hydroxypropyl, provided that $R_{18}$ and $R_{19}$ are not simultaneously hydrogen and, when $R_{18}$ and $R_{19}$ are each —$CH_2CH_2OH$, $R_{15}$ and $R_{16}$ are not simultaneously hydrogen and $R_{17}$ is not pentyl. These compounds are described in EP Patent specification 0 252 007.

Examples of viscosity-index improvers are
Polyacrylates, polymethacrylates, vinylpyrrolidone-/-methacrylate-copolymers, polyvinylpyrrolidones, polybutanes, olefin-copolymers, styrene-/-acrylate-copolymers, polyethers.

Examples of pour-point depressants are
Polymethacrylates, alkylated naphthalene derivatives.

Examples of dispersants/detergents are:
Polybutenylsuccinic acid-amides or -imides, polybutenyl-phosphonic acid derivatives, basic magnesium-, calcium-, and bariumsulfonates and -phenolates.

Examples of anti-wear additives and extreme pressure additives are:
Sulphur- and/or phosphorus- and/or halogen-containing compounds e.g. sulphurised vegetable oils, zinc dialkyldithiophosphates, tritolylphosphate, chlorinated paraffins, alkyl- and aryldi- and trisulphides, triphenylphosphorothionate.

The stabilizers of the instant invention have excellent hydrolytic stability. However, co-additives can optionally be employed to improve their hydrolytic stability still further. Examples of such co-stabilizers are:
Nitrogen containing compounds such as those described in U.S. Pat. Nos. 3,553,298 and 4,116,926, the disclosures of which are hereby incorporated by reference;
Long-chain aliphatic amines such as those disclosed in U.S. Pat. No. 4,650,894 and 4,707,509, the disclosures of which are hereby incorporated by reference; and
Organic acid metal salts such as those described in U.S. Pat. Nos. 4,086,304 and 4,402,858, the disclosures of which are hereby incorporated by reference.

The nitrogen compounds of particular interest are amines which have been shown to improve the hydrolytic stability of pentaerythritol spiro bis phosphites as taught in U.S. Pat. No. 4,888,371 where it is disclosed that an aliphatic, cycloaliphatic or heterocyclic amine as disclosed in U.S. Pat. No. 3,553,298 and 4,116,926 can be added to a spiro bis phosphite to improve hydrolytic stability.

Exemplary amines include, for example, trialkanolamines such as triethanolamine, triisopropanolamine and tri-n-propanolamine; dialkanolamines such as diethanol dodecylamine, diethanol octadecylamine, diethanol oleylamine, diethanol octylamine, diethanol hexadecylamine, diisopropanol dodecylamine, diisopropanol octadecylamine and di-n-propanol octadecylamine; dialkanolamines such as diisopropanolamine and diethanolamine; alkane-bis(dialkanolamines) such as ethylene-bis(diethanolamine) and ethylene-bis(diisopropanolamine); heterocyclic amines such as hexamethylenetetramine, piperidine, pyrrolidine, N-methylpiperidine, N-methylpyrrolidine, oxazolidine, morpholine and isooxazolidine; and amines oxides such lauryldimethylamine oxide and stearyldimethylamine oxide.

The preferred amount of the amine is from 0.01 to 5 parts by weight, preferably from 0.1 to 2 parts by weight, per 100 parts of spiro bis phosphite.

The following examples are presented for the purpose of illustration only and are not to be construed to limit the nature or scope of the instant invention in any manner whatsoever.

EXAMPLE 1

3,9-Bis(di-2-ethylhexylamino)-2,4,8,10-tetraoxa-3,9-diphosphaspiro[5,5]undecane

A flame-dried, 500 mL, 4 necked flask equipped with an overhead stirrer, thermometer, addition funnel and reflux condenser is charged with 10.7 g (40 mmol) of 3,9-di-chloro-2,4,8,10-tetraoxa-3,9-diphosphaspiro[5,-5]undecane and 250 mL of dry toluene under a dry nitrogen atmosphere. A mixture of 19.3 g (80 mmol) of di-2-ethylhexylamine and 8.1 g (80 mmol) of triethylamine at 0° C. is added dropwise to the stirred contents of the flask while the temperature is maintained below 5° C. with ice cooling. When the addition is complete, the mixture is warmed to ambient temperature and continually stirred until a filtered aliquot gives a negative Beilstein test (approximately 4 hours). The reaction mixture is then filtered to remove triethylamine hydrochloride and the filter cake is washed with two 25 ml portions of dry toluene. The combined filtrates are concentrated in vacuo to remove all volatiles to give 26.0 grams (96% yield) of the title compound as a colorless oil.

Analysis:
Calcd. for $C_{37}H_{76}N_2O_4P_2$: C, 65.8; H, 11.3; N, 4.1.
Found: C, 65.7; H, 11.7; N, 4.1.

EXAMPLE 2

3,9-Bis(N-methyl-N-octadecylamino)-2,4,8,10-tetraoxa-3,9-diphosphaspiro[5.5]undecane The procedure of Example 1 is repeated using 18.4 g (70 mmol) of 3,9-dichloro-2,4,8,10-tetraoxa-3,9-diphosphaspiro[5.5]undecane, 39.5 g (140 mmol) of N-methyl-N-octadecylamine and 19.5 mL (140 mmol) of triethylamine in 250 mL of toluene to give a crude reaction residue. The residue is purified by recrystallization from a mixture of toluene and acetonitrile to give 32 g (64% yield) of the title compound as an off-white solid melting at 70°–72° C.

Analysis:
Calcd. for $C_{43}H_{88}N_2O_4P_2$: C, 68.0; H, 11.7; N, 3.7.
Found: C, 67.7; H, 11.3; N, 3.6.

EXAMPLE 3

3,9-Bis(octadecylamino)-2,4,8,10-tetraoxa-3,9-diphosphaspiro[5.5]undecane

The procedure of Example 1 is repeated using 13.3 g (50 mmol) of 3,9-dichloro-2,4,8,10-tetraoxa-3,9-diphosphaspiro[5.5]undecane, 27.1 g (100 mmol) of octadecylamine and 15 mL (110 mmol) of triethylamine in 350 mL of toluene to give a crude reaction residue. The residue is purified by recrystallization from a mixture of toluene and acetonitrile to give 33 g (90% yield) of the title compound as an off-white solid melting at 67°–70° C.

Analysis:
Calcd. for $C_{41}H_{84}N_2O_4P_2$: N, 3.8.
Found: N, 3.7.

EXAMPLE 4

3,9-Bis(di(hydrogenated tallow)amino)-2,4,8,10-tetraoxa-3,9-diphosphaspiro[5.-5]undecane The procedure of Example 1 is repeated using 8.9 g (34 mmol) of 3,9-dichloro-2,4,8,10-tetraoxa-3,9-diphosphaspiro[5.5]undecane, 32.2 g (67 mmol) of di(hydrogenated tallow)amine (equivalent weight of 479) and 10.4 mL (75 mmol) of triethylamine in 800 mL of toluene to give 34.6 g (90% yield) of the desired product as a white wax: mp 24°–30° C.

Analysis:
Calcd. for $C_{77}H_{156}N_2O_4P_2$: N, 2.3.
Found: N, 2.3.

EXAMPLE 5

3,9-Bis(di-(tallow)amino)-2,4,8,10-tetraoxa-3,9-diphosphaspiro[5.5]undecane

The procedure of Example 1 is repeated using 8.6 g (32 mmol) of 3,9-dichloro-2,4,8,10-tetraoxa-3,9-diphosphaspiro[5.5]undecane, 30.0 g (65 mmol) of di-(tallow)amine (equivalent weight of 461) and 9.1 mL (65 mmol) of triethylamine in 1100 mL toluene to give 29.0 g (81% yield) of the desired product as a clear oil.

Analysis:
Calcd. for $C_{77}H_{148}N_2O_4P_2$: N, 2.3.
Found: N, 2.4.

EXAMPLE 6

Process Stabilization of Polypropylene at 260° C.

This example illustrates the stabilizing effectiveness of the instant stabilizers in combination with a representative phenolic antioxidant in old technology polypropylene as compared to other representative prior art compounds.

The base formulation comprises unstabilized, old technology polypropylene (PROFAX ® 6501, Hercules Chemical) containing 0.1% by weight of calcium stearate. The test additives are incorporated into the polypropylene by dry blending or, when the additive is a liquid, using a minimum amount of methylene chloride solvent, the solvent is then removed by evaporation under reduced pressure. The stabilized resin formulation is extruded at 100 rpm from a 1 inch (2.54 cm) diameter extruder at 260° C. with a residence time of 90 seconds.

During extrusion, the internal extruder pressure is determined using a pressure transducer. After each of the first and fifth extrusions, resin pellets obtained are compression molded into 125 mil (3.2 mm) thick plaques at 193° C. and specimen yellowness index (YI) determined by ASTM method D1925. Lower YI values indicate less discoloration.

After each of the first and fifth extrusions, the melt flow rate (in grams/10 minutes) is also determined by ASTM method D1238 condition L on the pellets obtained from the extruder. The melt flow varies inversely as the transducer pressure and both are measured of the molecular weight for the polymer.

The results are shown in the table below.

| Additive* (% by wt) | Transducer Pressure psig (Kg/cm$^2$) After Extrusion | | MFR (g/10 Min) After Extrusion | | YI Color After Extrusion | |
|---|---|---|---|---|---|---|
| | 1 | 5 | 1 | 5 | 1 | 5 |
| 0.1% AO A | 690 (48.3) | 480 (33.5) | 3.5 | 5.3 | 13.0 | 20.0 |
| 0.1% AO A plus 0.05% PS 1 | 810 (56.6) | 690 (48.3) | 3.9 | 6.8 | 7.3 | 13.0 |
| 0.1% AO A plus 0.05% compound of Example 1 | 825 (57.7) | 810 (56.6) | 3.1 | 3.1 | 4.3 | 6.2 |

*AO A is neopentanetetrayl tetrakis(3,5-di-tert-butyl-4-hydroxyhydrocinnamate).
PS 1 is 3,9-bis(di-n-octylamino)-2,4,8,10-tetraoxa-3,9-diphosphaspiro[5.5]undecane.

These results show that the instant compounds protect the polypropylene from discoloration far better than the phenolic antioxidant alone or than does the prior art stabilizer.

The instant compound of Example 1 provides outstanding resistance to discoloration as well as providing excellent stabilization against oxidative or thermal degradation as seen by transducer pressure and melt flow rate values. This is particularly surprising in view of the close structural relationship between the compound of Example 1 and PS 1.

EXAMPLE 7

This example illustrates the resistance to moisture pickup of the instant stabilizer as compared to other representative prior art compounds.

The test stabilizers are exposed to 80% relative humidity at 24° C. The moisture pickup is determined by monitoring the stabilizers for any change in weight after 10 days exposure (of after total hydrolysis). The results are shown below.

| Stabilizer* | Percent Weight Gain After 10 Days (or after total hydrolysis) |
|---|---|
| compound of Example 1 | 0.9 |
| compound of Example 4 | 0.6 |
| compound of Example 5 | 1.5 |
| prior art compound PS 2 | 4.2 (after 8 days) |
| prior art compound PS 1 | 2.0 |

*PS 1 is 3,9-bis(di-n-octylamino)-2,4,8,10-tetraoxa-3,9-diphosphaspiro[5.5]undecane.
PS 2 is 3,9-bis(di-n-butylamino)-2,4,8,10-tetraoxa-3,9-diphosphaspiro[5.5]undecane.

EXAMPLE 8

This example demonstrates the excellent resistance to hydrolysis of the instant stabilizers in contrast representative compounds of the prior art.

The test stabilizers are exposed to 80% relative humidity at 24° C. and their rate of hydrolysis is monitored by thin layer chromatography. The results are given as days to total hydrolysis as indicated by the disappearance of the original TLC spot. The results are tabulated in the table below.

| Stabilizer* | Days to Total Hydrolysis |
|---|---|
| compound of Example 1 | 77 |
| compound of Example 4 | 60 |
| Prior art compound PS 2 | 8 |
| Prior art compound PS 1 | 41 |

*PS 1 is 3,9-bis(di-n-octylamino)-2,4,8,10-tetraoxa-3,9-diphosphaspiro[5.5]undecane.
PS 2 is 3,9-bis(di-n-butylamino)-2,4,8,10-tetraoxa-3,9-diphosphaspiro[5.5]undecane.

Inspection of these data show that the instant compounds exhibit outstanding resistance to hydrolysis far superior to that of the prior art compounds.

EXAMPLE 9

Process Stabilization of Polypropylene at 525° F. (274° C.)

This example illustrates the stabilizing effectiveness of the instant stabilizers alone or in combination with a representative phenolic antioxidant in new technology polypropylene as compared to other representative prior art compounds.

The base formulation comprises unstabilized, new technology polypropylene (PROFAX® 6501, Ba 61834 Hercules Chemical) containing 0.075% by weight of calcium stearate. The test additives are incorporated into the polypropylene as described in Example 9. The stabilized resin formulation is extruded at 90 rpm from a 1 inch (2.54 cm) diameter extruder at 525° F. (274° C.) with a residence time of 90 seconds.

After each of the first, third and fifth extrusions, resin pellets obtained are compression molded into 125 mil (3.2 mm) thick plaques at 193° C. and specimen yellowness index (YI) determined by ASTM method D1925. Lower YI values indicate less discoloration.

After each of the first, third and fifth extrusions, the melt flow rate (in grams/10 minutes) is also determined by ASTM method D1238 condition L on the pellets obtained from the extruder. The melt flow rate is a measure of the molecular weight of the polymer and indicates whether thermal degradation is occurring during processing. A minimum change in melt flow rate indicates good process stabilization.

| Additive* (ppm) | Pellet YI Color | | | MFR | | |
|---|---|---|---|---|---|---|
| | 1 | 3 | 5 | 1 | 3 | 5 |
| none | 3.5 | 4.8 | 5.6 | 10 | 49 | 122 |
| compound of Example 1 (750) | 3.9 | 4.7 | 5.1 | 4.0 | 8.5 | 33 |
| prior art PS 1 (750) | 3.6 | 4.2 | 5.2 | 5.1 | 31 | 73 |
| AO A (750) | 6.5 | 8.0 | 9.6 | 7.1 | 9.0 | 12.3 |
| AO A (750) plus compound of Example 1 (750) | 4.2 | 5.7 | 7.9 | 2.7 | 2.9 | 3.9 |
| AO A (750) plus Prior art PS 1 (750) | 6.6 | 9.4 | 12 | 3.7 | 5.6 | 7.1 |

*AO A is neopentanetetrayl tetrakis(3,5-di-tert-butyl-4-hydroxyhydrocinnamate).
PS 1 is 3,9-bis(di-n-octylamino)-2,4,8,10-tetraoxa-3,9-diphosphaspiro[5.5]undecane.

This example illustrates the superiority of the instant compound of Example 1 for improving color and melt flow stabilization of new technology polypropylene alone or in combination with a representative phenolic antioxidant compared to a structurally closely related compound of the prior art.

EXAMPLE 10

Stabilization of Gasoline Engine Oils

The antioxidant effectiveness of the instant compounds in engine oils is measured by the Thin-Film Oxygen Uptake Test (TFOUT) designated by the ASTM D4742 method. A 1.5 gram test sample of 10W30 engine oil, formulated to meet the SD/CC quality level and containing 0.5% by weight of the test compound, is placed in the test apparatus. The test is then carried out according to the standard procedure and the oxidation induction time is minutes is measured. A longer induction time indicates a more effective antioxidant stabilizer. The instant compounds are effective antioxidant stabilizers for the engine oil.

What is claimed is:

1. A compound of formula I

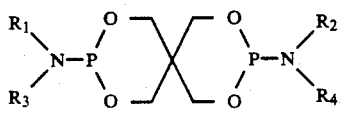

wherein $R_1$, $R_2$, $R_3$ and $R_4$ are each 2-ethylhexyl; or $R_1$, $R_2$, $R_3$ and $R_4$ are independently alkyl of 16 to 30 carbon atoms; or $R_1$ and $R_2$ are independently hydrogen or methyl, and $R_3$ and $R_4$ are independently alkyl of 16 to 30 carbon atoms; or $R_1$, $R_2$, $R_3$ and $R_4$ are independently a mixture of alkyl, alkenyl and alkadienyl radicals of 16 to 30 carbon atoms.

2. A compound according to claim 1 wherein $R_1$, $R_2$, $R_3$ and $R_4$ are independently hexadecyl, heptadecyl, octadecyl, eicosyl or tricontyl.

3. A compound according to claim 2 wherein $R_1$, $R_2$, $R_3$ and $R_4$ are independently hexadecyl, heptadecyl or octadecyl.

4. A compound according to claim 2 wherein $R_1$, $R_2$, $R_3$ and $R_4$ are the alkyl mixture found in hydrogenated tallow amine.

5. The compound according to claim 1 which is 3,9-bis[di-2-ethylhexyl)amino]-2,4,8,10-tetraoxa-3,9-diphosphaspiro[5.5]undecane.

6. A compound according to claim 1 wherein $R_1$, $R_2$, $R_3$ and $R_4$ are independently hexadecyl, heptadecyl, octadecyl, hexadecenyl, octadecenyl or octadecadienyl.

7. A compound according to claim 6 wherein $R_1$, $R_2$, $R_3$ and $R_4$ are the alkyl, alkenyl and alkadienyl mixture found in tallow amine.

8. A stabilized composition which comprises
   (a) an organic material, subject to thermal, oxidative or light-induced degradation, and
   (b) an effective stabilizing amount of a compound of formula I

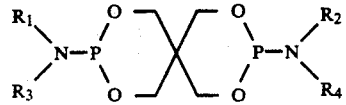

wherein $R_1$, $R_2$, $R_3$ and $R_4$ are each 2-ethylhexyl; or $R_1$, $R_2$, $R_3$ and $R_4$ are independently alkyl of 16 to 30 carbon atoms; or $R_1$ and $R_2$ are independently hydrogen or methyl, and $R_3$ and $R_4$ are independently alkyl of 16 to 30 carbon atoms; or $R_1$, $R_2$, $R_3$ and $R_4$ are independently a mixture of alkyl, alkenyl and alkadienyl radicals of 16 to 30 carbon atoms.

9. A composition according to claim 8 wherein the organic material of component (a) is an organic polymer or a lubricant or oil.

10. A composition according to claim 9 wherein the organic material of component (a) is an organic polymer.

11. A composition according to claim 10 wherein the organic polymer is a polyolefin or a polyamide.

12. A composition according to claim 11 wherein the polyolefin is polypropylene.

13. A composition according to claim 8 wherein the compound of formula I, $R_1$, $R_2$, $R_3$ and $R_4$ are independently hexadecyl, heptadecyl, octadecyl, eicosyl or tricontyl.

14. A composition according to claim 13 wherein $R_1$, $R_2$, $R_3$ and $R_4$ are independently hexadecyl, heptadecyl or octadecyl.

15. A composition according to claim 8 where the compound of formula I, $R_1$, $R_2$, $R_3$ and $R_4$ are the alkyl mixture found in hydrogenated tallow amine.

16. A composition according to claim 8 wherein the compound of component (b) is 3,9-bis(di-2-ethylhexylamino)-2,4,8,10-tetraoxa-3,9-diphosphaspiro[5.5]undecane.

17. A composition according to claim 8 wherein the compound of formula I, $R_1$, $R_2$, $R_3$ and $R_4$ are independently hexadecyl, heptadecyl, octadecyl, hexadecenyl, octadecenyl or octadecadienyl.

18. A composition according to claim 8 where in the compound of formula I, $R_1$, $R_2$, $R_3$ and $R_4$ are independently the alkyl, alkenyl and alkadienyl mixture found in tallow amine.

19. A composition according to claim 8 which additionally contains an effective stabilizing amount of a phenolic antioxidant.

20. A composition according to claim 19 wherein the phenolic antioxidant is selected from the group consisting of n-octadecyl 3,5-di-tert-butyl-4-hydroxyhydrocinnamate, neopentanetetrayl tetrakis(3,5-di-tert-butyl-4-hydroxyhydrocinammate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tertbutyl-4-hydroxyhydrocinnamate), 1,3,5-trimethyl-2,4,6-tris(3,5-di-tert-butyl-4-hydroxybenzyl)benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocynurate, 1,1,3,-tris(2-methyl-4-hydroxy-5-tert-butylphenyl)butane, 1,3,5-tris[2-(3,5-di-tert-butyl-4-hydroxyhydrocinnamoyloxy)ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)-ethyl]-oxamide.

21. A composition according to claim 20 wherein the phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)-benzene, 1,3,5-tris(3,5-di-tert-butyl-4-hydroxybenzyl)isocyanurate, 2,6-di-tert-butyl-p-cresol or 2,2'-ethylidene-bis(4,6-di-tert-butylphenol).

22. A composition according to claim 8 which additionally contains an effective stabilizing amount of a hindered amine.

23. A composition according to claim 22 wherein the hindered amine is selected from the group consisting of bis(2,2,6,6-tetramethylpiperidin-4-yl)sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dione, tris(2,2,6,6-tetramethylpiperidin-4-yl) nitrilotriacetate, 1,2-bis(2,2,6,6-tetramethyl-3-oxopiperazin-4-yl)ethane, 2,2,4,4-tetramethyl-7-oxa-3,20-diaza-21-oxodispiro[5.1.11.2] heneicosane, polycondensation production of 2,4-dichloro-6-tert-octylamino-s-triazine and 4,4'-hexamethylenebis(amino-2,2,6,6-tetramethylpiperidine), polycondensation production of 1-(2-hydroxyethyl-2,2,6,6-tetramethyl-4-hydroxypiperidine and succinic acid, polycondensation product of 4,4'-hexamethylenebis-(amino-2,2,6,6-tetramethylpiperidine) and 1,2-dibromoethane, tetrakis(2,2,6,6-tetramethylpiperidin-4-yl) 1,2,3,4-butanetetracarboxylate, tetrakis(1,2,2,6,6-pentamethylpiperidin-4-yl) 1,2,3,4-butanetetracarboxylate, polycondensation product of 2,4-dichloro-6-morpholino-s-triazine and 4,4'-hexamethylenebis(amino-2,2,6,6-tetramethylpiperidine), N,N',N'',N'''-tetrakis[(4,6-bis(butyl-2,2,6,6-tetramethyl-piperidin-4-yl)-amino-s-triazin-2-yl]-1,10-diamino-4,7-diazadecane, mixed [2,2,6,6-tetramethylpiperidin-4-yl/β,β,β',β'-tetramethyl-3,9-(2,4,8,10-tetraoxaspiro[5.5]-undecane) diethyl] 1,2,3,4-butanetetracarboxylate, mixed [1,2,2,6,6-pentamethylpiperidin-4-yl/β,β,β',β'-tetramethyl-3,9-(2,4,8,10-tetraoxaspiro[5.5]-undecane)diethyl] 1,2,3,4-butanetetracarboxylate, octamethylene bis(2,2,6,6-tetramethylpiperidin-4-carboxylate), 4,4'-ethylenebis(2,2,6,6-tetramethylpiperazin-3-one), and bis(1-octyloxy-2,2,6,6-tetramethylpiperidin-4-yl) sebacate.

24. A composition according to claim 23 wherein the hindered amine is bis(2,2,6,6-tetramethylpiperidin-4-yl) sebacate, the polycondensation product of 1-(2-hydroxyethyl)-2,2,6,6-tetramethyl-4-hydroxypiperidine and succinic acid, the polycondensation product of 2,4-dichloro-6-tert-octylamino-s-triazine and 4,4'-hexamethylenebis(amino-2,2,6,6-tetramethylpiperidine), N,N',N'',N'''-tetrakis[(4,6-bis(butyl-(2,2,6,6-tetramethyl-yl-piperidin-4-yl)amino)-s-triazine-2-yl]-1,10-diamino-4,7-diazadecane or bis(1-octyloxy-2,2,6,6-tetramethylpiperidin-4-yl) sebacate.

* * * * *